United States Patent [19]

Nakayama et al.

[11] Patent Number: 4,994,012
[45] Date of Patent: Feb. 19, 1991

[54] RADIATION-SHIELDED HOLDER FOR AN INJECTOR

[75] Inventors: Shozo Nakayama, Kobe; Mitsuhisa Iinuma, Nagoya; Hiroaki Matsushima, Nishinomiya, all of Japan

[73] Assignee: Nihon Medi-Physics Co., Ltd., Takarazuka, Japan

[21] Appl. No.: 349,430

[22] Filed: May 9, 1989

[30] Foreign Application Priority Data

May 9, 1988 [JP] Japan ............................ 63-61541[U]

[51] Int. Cl.$^5$ .............................................. A61B 6/00
[52] U.S. Cl. ........................................ 600/5; 128/654
[58] Field of Search ................ 600/3, 4, 5; 128/654; 604/187, 197, 199, 207

[56] References Cited

U.S. PATENT DOCUMENTS

| | | | |
|---|---|---|---|
| 3,673,414 | 6/1972 | Glasser | 600/5 |
| 4,048,997 | 9/1977 | Raghavachari et al. | 600/5 |
| 4,060,073 | 11/1977 | Collica et al. | 128/654 |

FOREIGN PATENT DOCUMENTS 3339817  6/1984  Fed. Rep. of Germany ...... 604/187

Primary Examiner—Kyle L. Howell
Assistant Examiner—K. M. Pfaffle
Attorney, Agent, or Firm—Jones, Tullar & Cooper

[57] ABSTRACT

A radiation-shielded injector comprises a cylinder of radiation shielding material having a cutout, a transparent radiation shielding plate being fitted to the cutout, a through-hole being provided at the closed end of the cylinder, a winged finger holding member being fixed to the cylinder, a cap having a hole for the passage through of a plunger being detachably attached, and a syringe-type body encapsulated with radioactive material, the cap being attached to the free end of the cylinder whereby the body is fixedly caught between the closed end of the cylinder and the cap. The infected is characterized by forming a built-up portion like a bank of radiation shielding material on the cutout periphery of the cylinder, the peripheral lateral side of the transparent plate being thereby covered with the thickness of the built-up portion. The radiation-shielded injector thus designed can minimize leakage of radiation and effectively protect the operator from radiation exposure.

2 Claims, 4 Drawing Sheets

RADIATION-SHIELDED HOLDER FOR AN INJECTOR

BACKGROUND OF THE INVENTION

1. Field of the Invention

The present invention relates to a radiation-shielded holder for an injector for administering a radioactive material, especially a radiopharmaceutical liquid, to a living body.

2. Description of the Prior Art

There is a syringe-type radiation-shielded injector for administering a radiopharmaceutical in medical treatment to a human body, which comprises, for example, as shown in FIG. 7, a lead cylinder 1 provided with a cutout extending on a peripheral wall in a lengthwise direction, a syringe-type cylindrical body 3 filled with a radiopharmaceutical inserted into the cylinder 1, and a transparent lead glass plate 2 fitted into the cutout so as to permit viewing the dosage scale of the inserted body 3, body 3 being held in place by pressure from a fixing screw member 4, wherein a syringe plunger (not shown) assembled to the body 3 can be operated to perform administration of the radiopharmaceutical to the patient while holding the cylinder 1 with one hand, thus protecting the operator's hand and body from radiation exposure.

However, if, in the above conventional radiation-shielded injector, the wall thickness of the cylinder 1 and the plate thickness of the glass plate 2 are adequately selected, shielding of the radiation emitted radially on the inner wall surface of the cylinder 1 and the inner surface of the glass plate 2 from the syringe-type body 3 can be sufficiently achieved as shown in alternate long and short dash lines in FIG. 7, but the radiation which transmits through the border between the cutout edge portion of the cylinder 1 and the glass plate 2 from the body 3 in the radial direction as shown in solid lines in FIG. 7 is shielded only with a thick-wall part of the wall thickness of the lead cylinder 1 and a part of the thickness of the glass plate 2, because of which considerable leakage of radiation occurs at the border part. The conventional injectors have a grave drawback in that the construction of shielding radiation cannot sufficiently protect the operator's hand and body from radiation exposure. On the other hand, it may be supposed to enlarge the diameter dimension of the lead cylinder or the thickness of the lead glass plate, but it is difficult to put such measures into practice because of the increase in the size and weight of the whole apparatus and the consequent deterioration of operating simplicity which is normally effected with one hand.

SUMMARY OF THE INVENTION

It is an object of the present invention to provide a radiation-shielded injector by which the abovementioned drawbacks can be completely eliminated and which can minimize leakage of radiation over the whole periphery of a radiation shielding cylindrical body, and yet without enlarging the resultant size of the apparatus.

In order to attain the above object, the radiation-shielded injector of the present invention is characteristically composed by forming a built-up portion like a bank on the cutout periphery of a radiation shielding cylinder and surrounding a peripheral lateral side of a transparent radiation shielding plate fitted to the cutout with the thickness of the built-up portion. The radiation shielding material to be used is preferably a tungsten metal so as to make the cylinder small in size and light in weight, and accordingly to effectively miniaturize the whole apparatus resulting in lighter weight.

BRIEF EXPLANATION OF THE DRAWINGS

These and other objects and features of the present invention will be hereinafter explained more in detail with reference to the accompanying drawings, in conjunction with preferred embodiments, throughout which like parts are designated by like reference numerals, and in which.

DETAILED DESCRIPTION OF THE PREFERRED EMBODIMENTS

Figure 5:
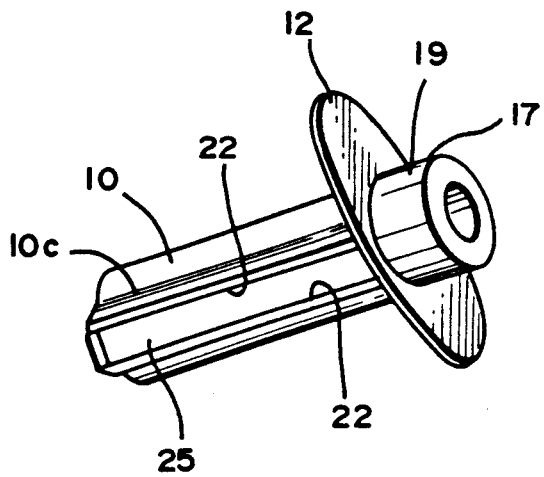
FIG. 5 is a perspective view of the injector part in an assembled state.

Referring more particularly to the various figures, a sinter molded cylinder 10 is made from a tungsten metal material having a high radiation shielding property. At one end 10a, referred to as the closed end 10a of the cylinder 10, a through-hole 11 is provided for passage through of the chip 31 of a syringe body 30 (FIG. 14), and at the other end 10b, referred to as the free or open end 10b a winged finger holder 12 and a cap 17 are attached. The 10b holder 12 and cap 17 are plastic molded parts. On the outer peripheral surface of the open end 10b of the cylinder 10, two positioning projections 13 are provided, and on the inner peripheral surface of the annular part of the holder 12, two recesses 14 are provided for correspondingly fitting with the projections 13, the cylinder 10 and the holder 12 being fixedly bonded together. Anti-slip ribs 15 are provided on the lower surfaces of the two winged parts 12a of the finger holder 12. The above cap 17 is provided with a hole 18 for passage through of the syringe plunger 39 (FIG. 6) to be described later, anti-slip notches 19 (FIGS. 5 and 6) on its outer peripheral surface and a female screw thread 20 on its inner peripheral surface. A male screw thread 16 corresponding to the female screw thread 20 of the cap 17 is provided on the outer periphery of the annular part 12b of the holder 12. The cap 17 is fitted to the annular part 12 b of the holder 12 by engaging the two screws 20 and 16.

Figure 1:
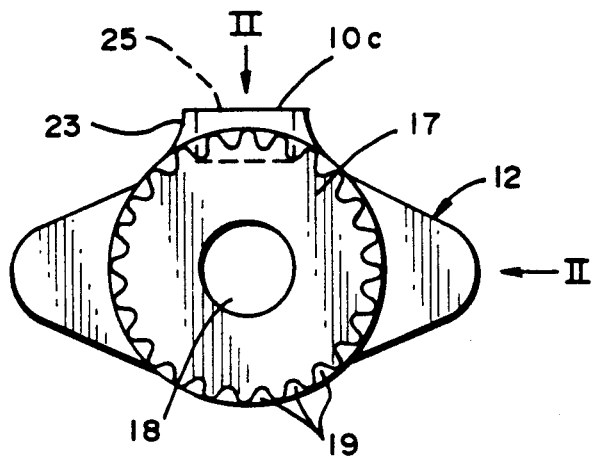
FIG. 1 is a plan view of the injector according to one embodiment of the present invention.
Figure 3:
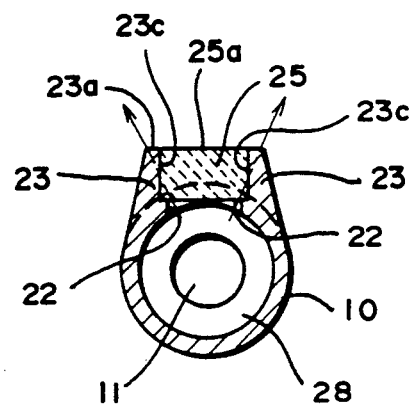
FIG. 3 is a cross-sectional view of the apparatus of FIG. 2 taken along the line III—III.
Figure 2:
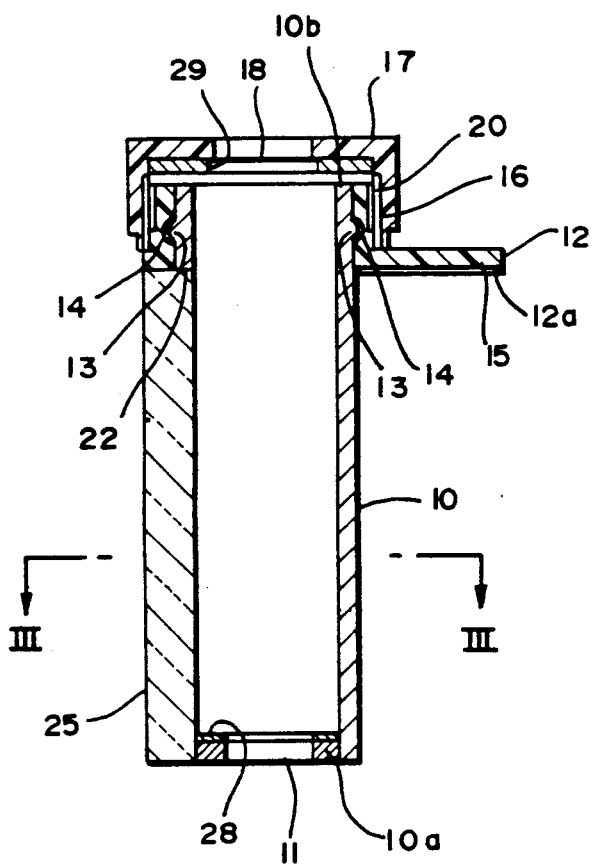
FIG. 2 is a sectional view of the apparatus of FIG. 1 taken along the line II—II.

On the peripheral wall of the cylinder 10, a rectangular cutout 22 extending in the lengthwise direction is formed and provided with a built-up portion 23 at the periphery of the cutout. Into the cutout 22, a rectangular transparent glass 25 having a high radiation shielding property, for example, of a lead glass material, is fitted, and the peripheral lateral side 23c of the glass plate 25 is bonded to the inner lateral side cf the built-up portion with an adhesive. The outer surface 24a of the glass plate 25 is set to be flush with the top 23a of the portion 23. The portion 23 is preferably made in the form of a bank having a gradually reduced wall thickness from its base toward its top, i.e., a tapered section. By this construction, the radiation emitted in the radial direction toward the borders between the portion 23 of the cylinder 10 and the glass plate 25 can be shielded with the same shielding effect as the radiation emitted to the thick wall parts other than the portion 23 of the cylinder 10. In other words, as shown in alternate two dots and one dash lines in FIG. 3, the resultant radiation shielding effect with a part of the glass plate 25 in the path of the radiation and a part of the portion 23 can be brought to nearly the same extent as that at the peripheral part of the cylinder 10 other than the portion 23. In other words, the specified radiation shielding ability can be obtained without unnecessarily enlarging the wall thickness of the portion 23 and accordingly without unduly increasing the weight of the cylinder 10.

To the face of the oven end 10b of the cylinder 10 and the inner face of the cap 17, there is fitted an annular packing 29. To the face of the closed end 10a there is fitted an annular packing 28. Also, a tapered part 27 is formed at the closed end of the outer periphery of the cylinder 10.

Figure 4:
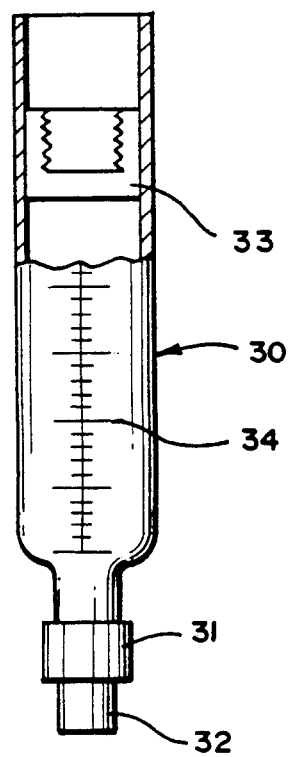
FIG. 4 is a partially cut sectional view of the syringe body applicable to the above injector.
Figure 6:
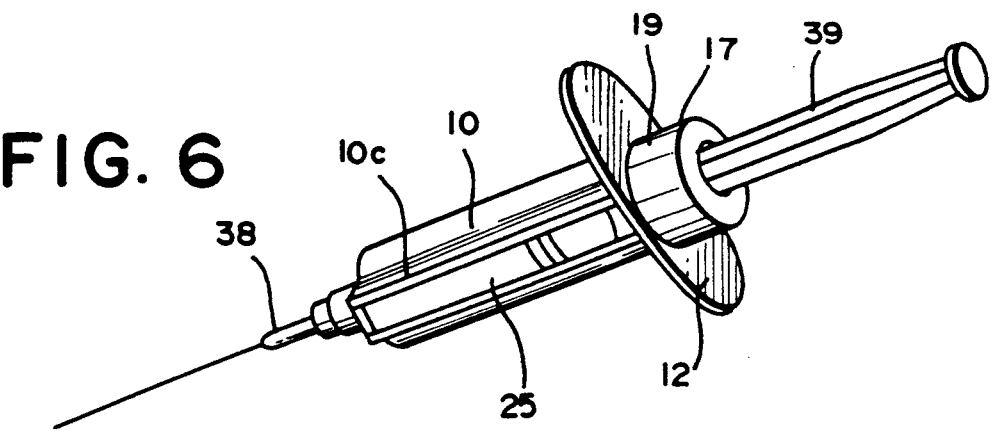
FIG. 6 is a perspective view of the injector in a completely assembled stage.
Figure 7:
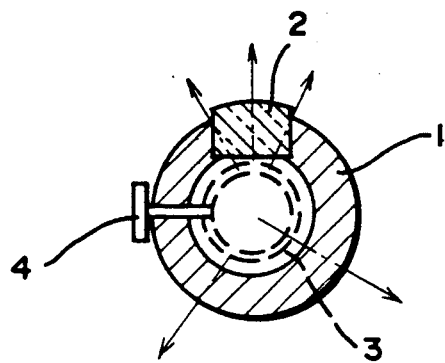
FIG. 7 is a schematic cross-sectional view illustrating the construction of the essential part of a conventional apparatus.
Figure 8:
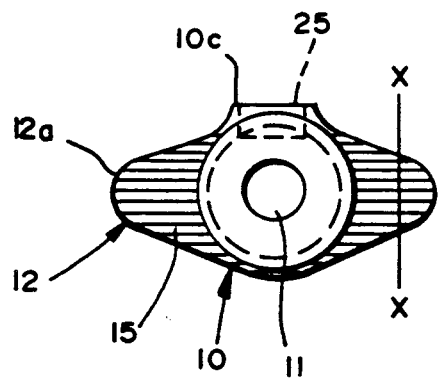
FIG. 8 is a plan view of the injector illustrating the anti-slip ribs.
Figure 9:
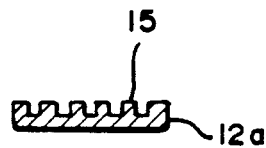
FIG. 9 is a cross-sectional view along the line X—X of FIG. 8.
Figure 10:
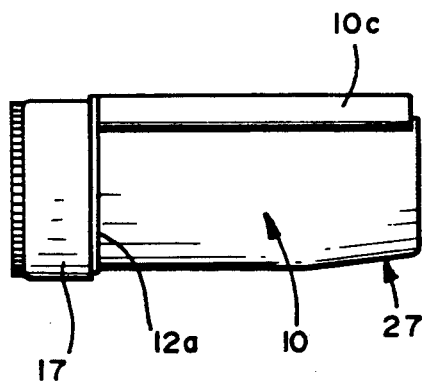
FIG. 10 is a schematic side view of the cylinder illustrating the tapered part.
Figure 11:
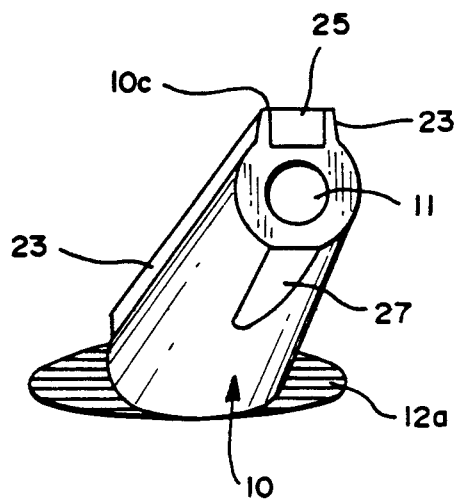
FIG. 11 is a perspective view of the cylinder also illustrating the tapered part and the anti-slip ribs.
Figure 12:
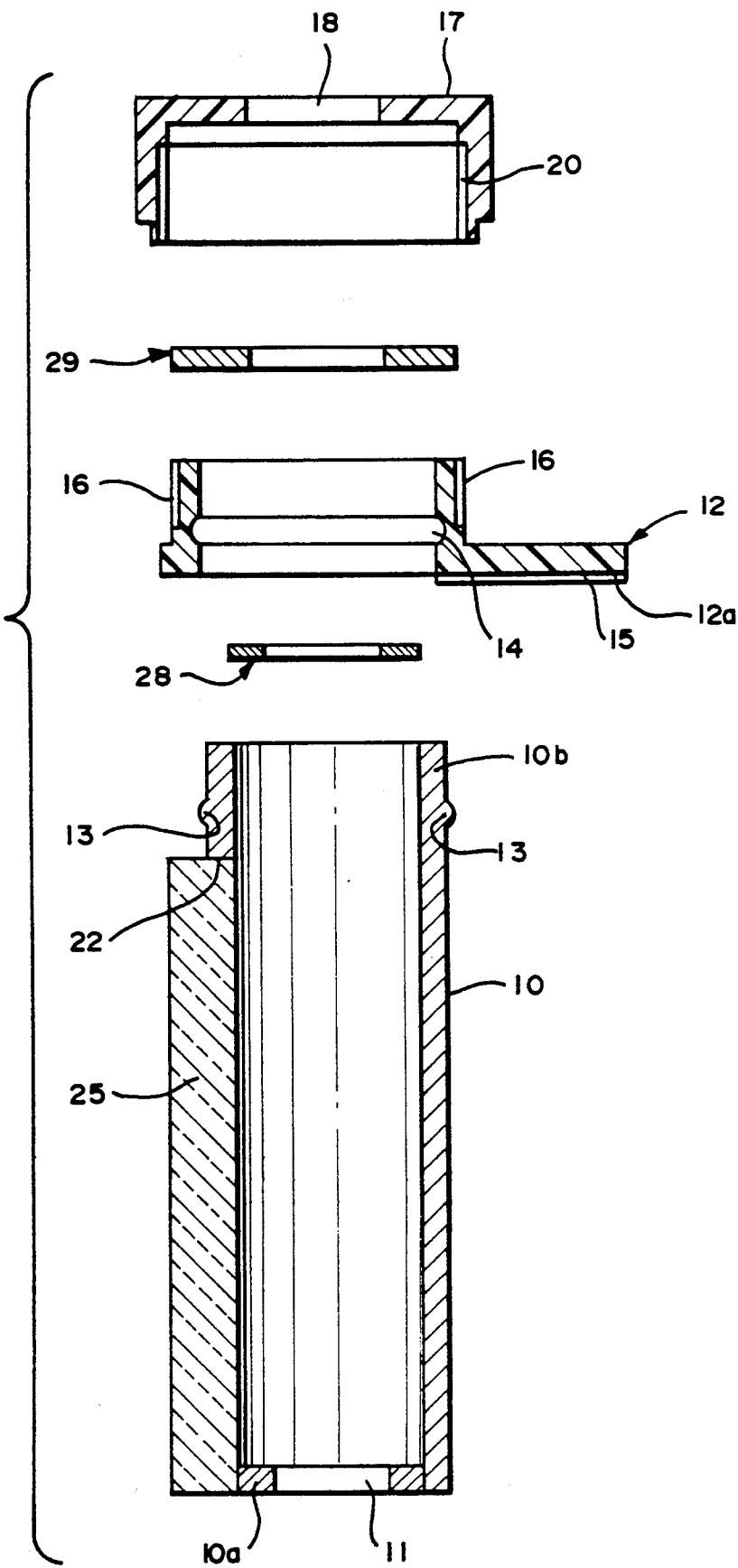
FIG. 12 is an exploded view in elevation of the cylinder.

FIG. 4 shows the syringe-type body 30 which is applicable to the injector of the present invention. The body 30 may be made of a suitable material selected from, for example, glass and synthetic resin so that it is usable as a so-called disposable syringe. The body 30 is filled with the required radiopharmaceutical liquid and sealed with a rubber cap 32 fitted into the chip 31 thereof, with the other end sealed with a piston or gasket 33 of elastic material. On operating the injector of the invention, as shown in FIG. 6, a commercialized double-sided injection needle 38 is fitted by a slip-on system to the chip 31 of the body 30, and, for example a plastic molded plunger 39 is fitted by threadedly engaging it to the piston 33.

In using the radiation-shielded injector of the above construction, firstly the syringe-type body 30 filled with a radiopharmaceutical is inserted into the open end 10b of the cylinder 10 and the chip 31 of the body 30 protrudes from the through-hole 11 at the closed end 10 b. Then, the cap 17 is fixed by screwing to the annular part 12b of the holder 12. Next, the plunger 39 is inserted through the hole 18 of the cap 17 and fixed by threadedly engaging it to the piston 33, and further the cap 32 attached to the chip 31 of the body 30 is removed and the injection needle 38 is fitted to the clip 31 as noted above. By this procedure, the preparation for use of the apparatus is completed.

The operator may perform the injection operation by applying the two fingers of one hand to the lower surfaces of the two wings parts 12a of the holder 12 of the above assembly unit and the thumb thereof to the front end of the plunger 39 and pressing the plunger 39 while viewing the dosage scale 34 on the body 30 through the window formed by the transparent lead glass plate 25.

According to the injector of the present invention having the above construction, a built-up portion like a bank is provided at the peripheral part of the cutout of the radiation shielding cylinder, so that it is possible to effectively protect against radiation exposure which, coming from the syringe-type body in the cylinder, transmit through the border between the periphery of the cutout and the outer periphery of the radiation shielding plate to the same extent as the portions other than the built-up portion. Accordingly, it is possible to minimize radiation leakage as produced in the conventional type apparatuses and certainly protect the operator from radiation exposure.

Especially, by forming the above built-up portion like a bank having a tapered section, radiation leakage from the whole outer periphery of the cylinder can be effectively and certainly prevented without an increase in weight of the whole apparatus.

Further, if the above cylinder is made of a tungsten metal material having high radiation shielding properties, reduction in size of the apparatus can be effectively achieved.

What is claimed is:

1. A radiation-shielded holder for an injector, comprising:
  a cylinder of radiation shielding tungsten, said cylinder being provided with a circular bore for inserting a cylindrical syringe-type body, and a protruding portion having a quadrilateral cross section which protrudes from a peripheral side of said cylinder, the protruding portion comprising a cutout extending in the lengthwise direction of said cylinder, wherein said protruding portion is a built-up portion of said radiation shielding tungsten which is formed on the cutout periphery of said cylinder, the body having a piston and a plunger screwed onto the piston, a space encapsulating radioactive material being defined by said body and the piston;
  a transparent radiation shielding plate being fitted to the cutout, of which a peripheral lateral side is covered with the built-up portion;
  a through hole being provided at one end of said cylinder;
  a winged finger holding member being fixed to the other end of said cylinder, said holding member having an annular part, the cutout extending from one end of said cylinder which has said through hole to the vicinity of a portion where said member is fixed to said cylinder;
  a cap having a hole for passage through of a plunger, said cap being detachably screwed onto the annular part of said holding member;
  a first annular packing arranged between said cap and the annular part of said holding member and capable of contacting with the body; and
  a second annular packing arranged around a periphery of the through hole on the end of said cylinder and capable of contacting with the body;
  wherein when the body is inserted into the bore of said cylinder, a tip of the body projects from said through hole at said one end, while said cap is screwed onto said member which is fixed to the other end of said cylinder, whereby the body is fixedly caught between said one end and said cap.

2. The radiation-shielded holder according to claim 1, wherein the built-up portion comprises a banked section which tapers from its base toward its top.

* * * * *